United States Patent [19]

Swart

[11] Patent Number: 4,959,538

[45] Date of Patent: Sep. 25, 1990

[54] INSPECTION DEVICE

[75] Inventor: Nicolaas C. Swart, Deventer, Netherlands

[73] Assignee: Heuft-Qualiplus B.V., Netherlands

[21] Appl. No.: 328,297

[22] Filed: Mar. 24, 1989

[30] Foreign Application Priority Data

Apr. 5, 1988 [NL] Netherlands .......................... 8800866

[51] Int. Cl.⁵ .............................................. G01N 9/04
[52] U.S. Cl. ................................. 250/223 B; 356/240
[58] Field of Search ..................... 250/223 B; 356/240; 209/524

[56] References Cited

U.S. PATENT DOCUMENTS 4,701,612 10/1987 Sturgill ................................. 356/240
4,758,084 7/1988 Tokumi ................................ 356/240

Primary Examiner—David C. Nelms
Assistant Examiner—Sherrie Hsia
Attorney, Agent, or Firm—Watson, Cole, Grindle & Watson

[57] ABSTRACT

The mouth edges of a succession of bottles can be inspected using a lighting system for lighting the mouths of each bottle, an optical imaging system for forming an image of the mouth of each bottle, a measuring system for determining the height of the mouth of each successive bottle, and a movable lens in the optical imaging system for compensating for differences in mouth heights of the bottles.

15 Claims, 3 Drawing Sheets

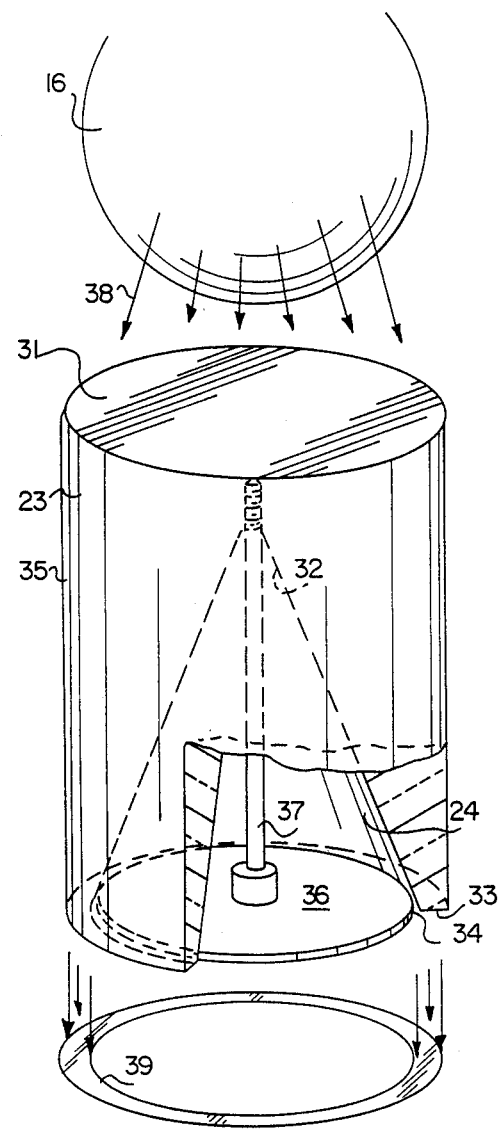

INSPECTION DEVICE

BACKGROUND AND SUMMARY OF THE INVENTION

The invention relates to a device for inspecting the upper surfaces of successive objects, for instance the mouth edges of glass bottles carried by a conveyor belt and guided thereby past the device, which device is provided with an optical system, comprising:

a lighting system with a light source for lighting an upper surface of each object, and an optical imaging system for forming in each case an image of an upper surface.

Such a device is known in diverse embodiments. The articles for inspection, for example glass bottles, may, as a result of the nature of the production process, have mutual height differences. These height differences can cause problems with respect to the automatic visual inspection of the bottle mouth. A bottle inspection device is known for instance in which the height difference is levelled out by grasping each bottle under the flanged edge or neck that protrudes sideways at the top. Small differences in height can be evened out in this way.

If the height differences are not evened out or are inadequately evened out, the optical path length from the light source to the image of the upper edge will not be the same for each bottle. As a result, the setting of an inspection system cannot be carried out optimally. A consequence of this positional inaccuracy is that accuracy of inspection has to be sacrificed.

The invention has for its object to embody a device of the type described such that the above stated problem is solved.

The invention also aims to embody a device of the noted type such that it can be added to an existing conveyor device, for instance a bottle conveyor.

A further object of the invention is to provide a device which enables a very compact construction.

Finally, the invention aims to embody an inspection device such that great flexibility is achieved, and such that it always operates reliably, irrespective of the mutual interval between the objects.

Generally, the invention provides a device of the above described type that is characterized by:

measuring means for measuring the height of one edge at a time, and adjustment means for setting the optical system on the basis of the height of an edge as determined by the measuring means.

A very simple embodiment is one in which the adjustment means comprise an optical element displaceable along the optical axis. Such an optical element can be given a lighter form than a light source and is moreover a passive element so that difficulties with cables are not encountered.

In a very simple embodiment the optical element comprises a lens.

In order to obtain an intensive lighting for the inspection of bottle mouths or other annular reflecting surfaces, use is preferably made of a ring-shaped light source. Such a light source is per se known, for instance in the form of annularly arranged outer ends of light conductors coupled to a light source.

Preference is given, however, within the scope of the invention to an embodiment of the lighting system that not only functions as ring-shaped light source but also emits as much directed light as possible to the annular surface for inspection, this in order to prevent masking of faults, which can occur in the case of radiation with non-directed light. In this respect the invention provides a device displaying the feature that the optical element comprises a transparent block, which block is cylinder-shaped, has an entry surface facing the light source, comprises a conical hollow, the top of which is directed to the entry surface, and has an exit surface extending in the form of a ring between the base of the hollow and the cylinder surface. In this embodiment the block functions as light conductor, as a result of which the light falling in on the entry surface is generated with very high yield via the exit surface.

In order to prevent undesired exit of light via the cylinder surface and/or the cone surface an embodiment can be used in which the cylinder surface and/or the cone surface is provided with a mirror.

If desired the block can be embodied such that the exit surface is diffusely transparent, for example is matted or provided with an opal covering layer. Using such an embodiment the directional preference of the outgoing light, if any, is reduced to negligible proportions.

In order to avoid spurious light possibly being generated via the cone surface an embodiment can serve in which a screen not allowing passage of light is situated in the base of the cone. The block can in this case be embodied such that a fastening member is fixed in position in the block through the top of the cone.

In a very simple embodiment the optical element comprise a lens. This lens may be an objective lens of a video camera for instance so that in accordance with the invention, focussing of the camera takes place on the basis of the measured height of the surface for measuring.

In order to obtain the best possible image of the surface for inspection, the variant is recommended in which the lighting system is arranged for emitting a light bundle concentrated on the surface for lighting. In particular the device can in this case be characterized by a ring-shaped mirror adapted to the shape of the surface for illumination, which mirror concentrates light coming from the light source on the upper surface for illumination.

For the inspection of an annular upper surface of objects, in particular the round mouths of bottles, the device can in this latter case display the feature that the ring-shaped mirror possesses the form of the surface of a frustum cone, the centre line of which coincides with the optical axis of the lighting system.

In a practical embodiment the device has the feature that the measuring means comprise a row of photo-cells. This row of photo-cells can form part of a linear-array camera.

The invention further relates to a transparent block, as specified in the foregoing. This block can serve as light conductor for the concentrating of light concentrated on the entry surface onto the ring-shaped exit surface.

The invention will now be elucidated with reference to the annexed drawings.

BRIEF DESCRIPTION OF THE DRAWINGS

FIG. 3 shows a partly broken away perspective view of a perspex block with a conical hollow, which block serves as light conductor for the forming of an intensive ring-shaped light source.

DETAILED DESCRIPTION OF THE PREFERRED EMBODIMENT

Figure 1:
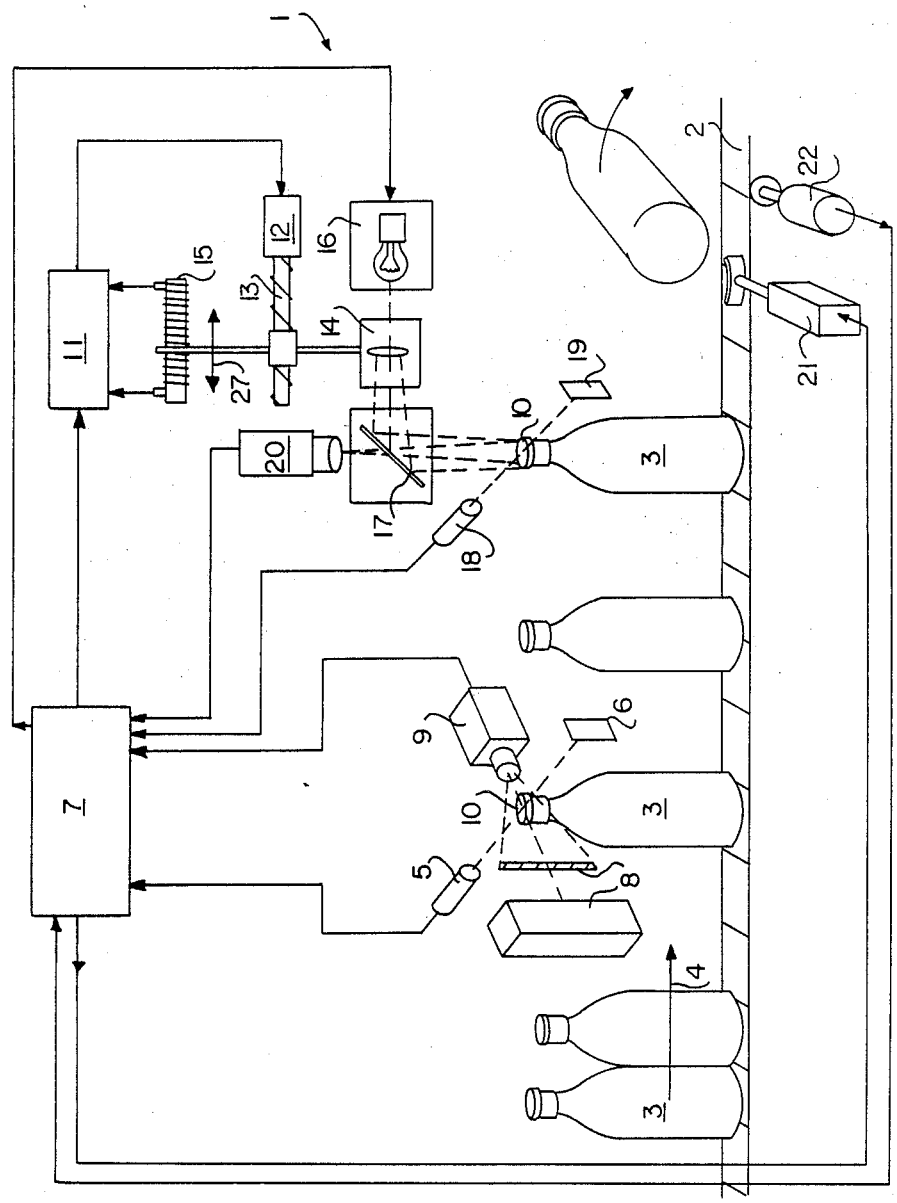
FIG. 1 is a schematic representation of an inspection device according to the invention in a first embodiment.

FIG. 1 shows an inspection device 1 disposed along a conveyor belt 2 which is driven by suitable means (not shown) and which transports a succession of bottles 3 in the direction of an arrow 4. A light source with photo-cell 5 sends light to a reflector 6 and receives light reflected therefrom. When the light beam is broken by the arrival of a bottle 3, a trigger signal is generated to a central processor unit or CPU 7. A light source 8 illuminates the thus-detected bottle 3, as a result of which a linear array camera 9 arranged on the other side of this bottle 3 can feed a height signal to the CPU 7, this height signal being a measure for the height of the mouth 10 of bottle 3. The CPU 7 feeds this height signal to a servo-device 11 which supplies a servo-motor 12 with a corresponding energizing signal such that a spindle 13 is set into rotation. Coupled to this spindle is a lens unit 14 as well as a position recorder 15 which returns a position signal corresponding to the position of the lens unit 14 to the servo-device. A comparison of this position signal with the height signal by the servo-device 11 determines in a generally known manner the end position of lens unit 14.

Via the lens unit 14 and a semi-transparent mirror 17 a light source 16 can light the bottle mouth 10 of a bottle 3 that has arrived at that location. Arrival of this bottle 3 is again detected by a light source/photo-cell 18 and the reflector 19. When the relevant light beam is broken this photo-cell passes on a trigger signal to the CPU 7, which then energizes the light source 16 in the form of a flash bulb in order to generate a flash.

A video camera 20 observes the bottle mouth 10 via the semi-transparent mirror 17, forms an image thereof and transmits a video signal corresponding to that image to the CPU 7. On the basis of approval/rejection criteria a rejection signal may be generated in the CPU 7 and fed to a pusher member 21 which pushes a rejected bottle from the conveyor belt 2 when it is actuated.

The CPU 7 further comprises decelerating means which must ensure that each bottle is identified unmistakably so that the setting of the lens unit 14 is used for the correct bottle 3 measured by the unit 5, 6, 8, 9. After passing the station 16, 14, 17, 18, 19, 20 a rejected bottle has to be removed by the pusher member 21 following a suitable deceleration subject to the speed of conveyor belt 2. A tachogenerator 22 measures the speed of the conveyor belt 2.

Figure 2:
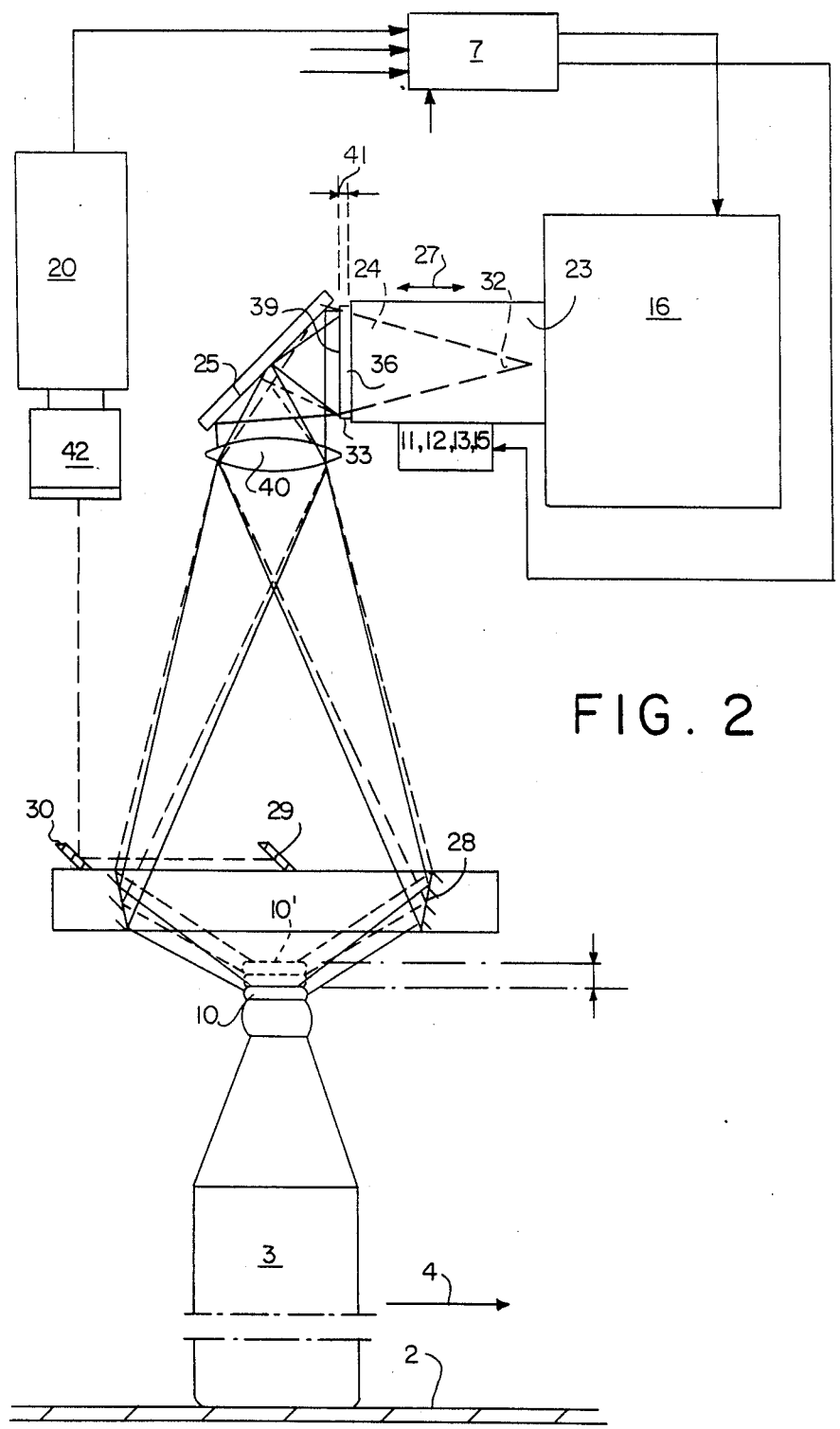
FIG. 2 is a highly simplified schematic representation of a variant.

FIG. 2 shows schematically a preferred embodiment. This diagram comprises a CPU 7 which is embodied in principle in the same manner as described briefly in FIG. 1. The description given there of height measurement will not be repeated here.

The light source 16 in the form of flash bulb or stroboscope lamp sends its light to a light conductor in the form of a perspex block 23 (see the more detailed FIG. 3), which block is cylinder shaped and has an entry surface facing the light source 16, comprises a conical hollow 24, of which the top 32 is directed to the entry surface 31, and has a ring-shaped exit surface 33 extending between the base or bottom surface 34 of the conical hollow and the end of the cylinder surface 35 adjacent thereto.

Located in the base 34 is a screen 36 not allowing the passage of light supported by a rod 37 which is screwed into position through the top 32 of the conical hollow 24 into the block 23.

The light source 16 emits light to the entry surface 31 in the manner indicated by arrows 38. This light travels via block 23 and is generated via the matt exit surface 33, which can thus function as intensive, ring-shaped light source. This ring-shaped light source is indicated symbolically in FIG. 3 and designated with the reference numeral 39.

The light originating from the source 39 is reflected by a mirror 25 which is disposed at 45°. A lens system 40, drawn here as a single lens, forms an image of the light source 39 such that via a ring-shaped mirror 28 with the form of the surface of a frustum cone, it is imaged onto the mouth of a passing bottle 3 for inspection. The reflected light is directed onto the mouth 10 of the bottle 3 and the light reflected therefrom is fed via mirrors 29, 30 to the video camera 20.

Shown with full lines is the mouth 10 of a bottle 3 to which the device is adjusted in this situation.

A mouth 10' is of another bottle 3 and is situated at a greater height than the mouth 10 of the bottle 3. Drawn with broken lines is the beam path that the light transmitted by the source 39 now has to follow in order to be directed onto this mouth 10'. The positional alteration of the ringshaped light source 39 necessary for this purpose is indicated with 41. This alteration of position is effected in a manner analogous to that described with reference to FIG. 1 by prior measurement of the height of mouth 10' and the corresponding displacing of the perspex block 23 by means of a control mechanism that is embodied in a form wholly analogous to that of the units 11, 12, 13, 15 as in FIG. 1. It is hereby noted that the control of this servo-device 11, 12, 13, 15 takes place in the CPU 7 such that the imaging of the ring-shaped light source 39 is indeed effected at the correct height within the set tolerances. It is remarked that in the embodiments described it is not a matter of accurate adjustment of the objective 42 of video camera 20 on the desired surface. Use is therefore made in these embodiments of a "mean" setting, whereby it is noted that inspection can then only be performed reliably if the variations in height of the passing bottle mouths remain located within the depth of field of the video camera 20 with the objective 42. It will otherwise be apparent that, if required, the CPU 7 can supply a control signal to the video camera 20 for accurate focussing thereof on the mouth for inspection.

The frustum conical mirror 28 can for example take the form of a vapour-deposited aluminium layer on a correspondingly shaped surface of a plate, for instance of perspex. Use can also be made of a metal block, for instance of aluminium, in which the mirror 28 is formed by a machining process.

Finally, attention is drawn to the fact that it could be desirable, depending on the type of light source 16 used, to give the entry surface 31 of block 23 a specific form, thus enabling a further increase in the effectiveness of this block as light conductor.

It will be apparent that the embodiments shown and described serve only by way of explanation of the principle of the invention; optical elements other than the elements 14, 23 could be movable via a servo-system of the type described, whereby the same effect as described above is achieved.

I claim:

1. Device for inspecting the upper surfaces of successive objects, for instance the mouth edges of glass bottled carried by a conveyor belt and guided past the device thereby, which device is provided with an optical system, comprising:
    a lighting system with a light source for lighting an upper surface of each successive object,
    an optical imaging system for forming an image of an upper surface of each successive object,
    measuring means for measuring the height of the upper surface of each successive object, and
    adjustment means for setting the optical system on the basis of the height of the upper surface of each successive object as determined by said measuring means.

2. Device as claimed in claim 1, wherein the adjustment means comprise an optical element and a drive means for moving the optical element along an optical axis.

3. Device as claimed in claim 2, wherein the optical element comprises a lens.

4. Device as claimed in claim 3, wherein the optical element comprises a transparent block which
    is cylinder-shaped,
    has an entry surface facing the light source,
    comprises a conical hollow, the top of which is directed to said entry surface, and
    has an exit surface in the form of a ring extending between the base of the hollow and the cylinder surface.

5. Device as claimed in claim 4, wherein at least one of the cylinder surface and the cone surface is mirrored.

6. Device as claimed in claim 4, wherein the exit surface is diffusely transparent.

7. Device as claimed in claim 4 wherein a screen not allowing passage of light is situated in the base of the cone.

8. Device as claimed in claim 7, wherein the screen is fixed in position by means of a fastening member into the block through the top of the cone.

9. Device as claimed in claim 1, wherein the lighting system is arranged to emit a light bundle concentrated on the upper surface of each successive object.

10. Device as claimed in claim 9, characterized by a ring-shaped mirror adapted to the shape of the surface for illumination, which mirror concentrates light coming from the light source on the upper surface of each successive object for illumination.

11. Device as claimed in claim 10 for the inspection of an annular upper surface of objects, in particular the round mouths of bottles wherein the ring-shaped mirror possesses the form of the surface of a frustum cone, the centre line of which coincides with optical axis of the lighting system.

12. Device as claimed in claim 1 wherein the measuring means comprise a row of photo-cells.

13. Device as claimed in claim 6, wherein said exit surface is matted.

14. Device as claimed in claim 6, wherein said exit surface has an opal covering layer thereon.

15. A transparent cylindrical block capable of functioning as a ring-shaped light source, said cylindrical block defining a first end surface through which light can enter the block and a second end surface through which light can exit the block, said block defining a blind conical hollow chamber therein which extends from said second end surface towards said first end surface, such that said second end surface is ring shaped.

* * * * *